United States Patent [19]

Geiser et al.

[11] Patent Number: 5,426,505
[45] Date of Patent: Jun. 20, 1995

[54] INTERFEROMETRIC APPARATUS FOR MONITORING CHANGES OF THE REFRACTIVE INDEX OF FLUID SAMPLES IN CAPILLARY TUBES

[75] Inventors: Martial Geiser, Sion; Hans P. Herzig, Neuchâtel; Beat Krattiger, Riehen; Alfredo E. Bruno, Oberwil, all of Switzerland

[73] Assignee: Ciba-Geigy Corporation, Ardsley, N.Y.

[21] Appl. No.: 154,205

[22] Filed: Nov. 18, 1993

[30] Foreign Application Priority Data

Nov. 25, 1992 [EP] European Pat. Off. ........ 92810915.6

[51] Int. Cl.⁶ .............................................. G01B 9/02
[52] U.S. Cl. .................................... 356/361; 356/354; 356/128
[58] Field of Search ............... 356/361, 128, 246, 354, 356/353; 359/15

[56] References Cited

U.S. PATENT DOCUMENTS

| | | | |
|---|---|---|---|
| 4,421,409 | 12/1983 | Dickey et al. | 356/354 |
| 4,993,832 | 2/1991 | Pawliszyn | 356/128 |
| 5,074,666 | 12/1991 | Barnes et al. | 356/361 |
| 5,153,666 | 10/1992 | Pawliszyn | 356/128 |
| 5,251,009 | 10/1993 | Bruno | 356/361 |
| 5,312,535 | 5/1994 | Waska et al. | 356/344 |

FOREIGN PATENT DOCUMENTS 2228995  9/1990  United Kingdom .

OTHER PUBLICATIONS

L. H. Tanner—J. Sci. Instrum., vol. 43 pp. 878–885, (1966).
A. E. Bruno, et al., Anal. Chem. vol. 63 pp. 2689–2697, (1963).
Inspec. AN-2619083, Japanese Journal of Applied Physics, Part 2 (Letters) Sep. 1985, pp. L739–L741, T. Hoshimiya.
Derwent Abst. 89-222916.

Primary Examiner—Samuel A. Turner
Attorney, Agent, or Firm—George R. Dohmann

[57] ABSTRACT

An interferometric apparatus for monitoring changes of the refractive index of An interferometrilcapillary tubes comprising a source of coherent light, which is arranged with respect to a capillary tube which is part of a capillary liquid chromatographic system or a capillary electrophoretic system, such that the coherent light beam strikes the capillary tube about perpendicular to its longitudinal extension. In the forward direction of the coherent light beam, behind the capillary tube, the apparatus comprises a photoelectric detector for monitoring a resulting interference fringe pattern and the shifts thereof, which is connected to an evaluation electronics. Between the light source and the capillary tube there is arranged a beam splitting optical element for generating a converging probe beam, which travels along a probe beam axis and strikes the capillary tube at its bore, and a converging reference beam, which travels along a reference beam axis, that extends generally parallel to the probe beam axis and is located in close vicinity to the probe beam axis, and which does not strike the capillary bore.

16 Claims, 2 Drawing Sheets

INTERFEROMETRIC APPARATUS FOR MONITORING CHANGES OF THE REFRACTIVE INDEX OF FLUID SAMPLES IN CAPILLARY TUBES

BACKGROUND OF THE INVENTION

The invention relates to an interferometric apparatus for monitoring changes of the refractive index of fluid samples in capillary tubes, in particular to a refractive index based measurement system used for example in capillary liquid chromatography or capillary electrophoresis.

In modern analysis of chemical samples there exists a great demand for techniques involving only a small volume of the test sample. Capillary liquid chromatography and capillary electrophoresis belong to the most exciting and potentially useful microvolume separation techniques. Among the most important features of these new instrumental techniques are high peak resolution, short analysis time, and the minimal amounts of test sample required. The total column volume in these new techniques amount to as little as only a few microliters, and the required sample volumes are in the nanoliter or even in the picoliter range. Various instrumental aspects of these capillary-based, fluid-phase separation schemes contribute to the overall system performance. A major instrumental limitation of the performance of these techniques is the lack of highly sensitive microvolume detectors and the fact, that the so-called "off-column" detection, where the separated bands of the test sample are transferred to the detection cell, is associated with unwanted re-mixing effects.

As a solution to the problems associated with the "off-column" detection these capillary-based techniques employ so-called "on-column" detection methods, which do not distort the spatial profile of the eluting peaks. Among these "on-column" detection methods the monitoring of changes of the refractive index of the fluid test sample proves to be most promising. This technique is based on tile detection of tile phase shift of a coherent light beam passing through the fluid test sample, which occurs due to refractive index changes of the test sample with respect to the carrier buffer or the solvent contained within the capillary tube. The method makes use of the fact, that the phase shifts of the light beam transversing the fluid test sample flowing through the capillary tube are linearly related to the changes of the refractive index of the test sample.

For monitoring the changes of the refractive index of the test sample in capillary tubes a refractive index measurement system has been developed. The refractive index measuring system consists basically of an interferometer, having a source of coherent light, which is directed at the capillary tube, a photoelectric detector, and an evaluation electronics. The light beam, usually coming from a laser source, strikes the capillary tube; part of the light beam transverses the flowing path of the test sample and interacts with the test sample; whereas part of the light beam is reflected at the glass walls of the capillary. Thus, the light beam is split at the capillary tube, more specifically at its inner optical interface, into a probe beam and into a reference beam having a phase difference, which upon recombination of the two beams results in a generally asymmetric interference fringe pattern in the far field. The interference fringe pattern is measured by the photoelectric detector in the forward direction of the probe beam, and shifts laterally as the refractive index of the test sample flowing through the capillary tube changes.

Refractive index measuring systems of the kind described before are known from the prior art. The performance of these measuring systems was distinctly increased by arranging the capillary tube within material, which matches or almost matches the refractive index of the material the capillary tube is made from, as described in an article by A. E. Bruno, B. Krattiger, F. Maystre and H. M. Widmer, Anal.Chem., 1991, 63, page 2689–2697. In doing so, the boundary optical interfaces, which the laser beam encounters upon its propagation along the light path and striking the capillary tube, are reduced, the interference fringe pattern becomes more simple and easier to evaluate, and the signal/noise ratio is enhanced. In spite of the good results, which are achieved with the thus improved refractive index measuring systems known from the prior art, these devices still can be further improved. In case the capillary tube is not surrounded by a matching material, the resulting interference fringe pattern is rather complex and cannot be reliably evaluated and interpreted. Also, irregularities on the boundary surfaces of the capillary tube may modify the reference beam in an unexpected way.

OBJECTS OF THE INVENTION

In micro-analysis there exists a great demand for detection methods, which need only very little test sample volumes. It is also known, that the separation efficiency is increased if capillary tubes with very small internal diameters are used as separation columns. However, the mere replacement of the usually applied capillary tubes having internal diameters ranging from for example 50 $\mu$m up to for example 500 $\mu$m, with capillary tubes having internal diameters of 25 $\mu$m and even less, in a refractive index measuring system, results in a degradation of the instrument's performance.

It is therefore an object of the present invention to provide an interferometric apparatus for monitoring changes of the refractive index of fluid samples, in particular a refractive index measurement system used for example in capillary liquid chromatography or capillary electrophoresis, which overcomes the drawbacks of the interferometric apparatus known from the prior art. The invention shall provide an interferometric apparatus, which allows it to be used with capillary tubes having internal diameters of 25 $\mu$m and even less. The sensitivity of the produced interference fringe pattern with respect to refractive index changes of the test sample shall be identical for all fringes. The fringes shall be equally displaced, and displacement shall occur in one direction only. The invention shall provide an interferometric apparatus, in which all of the light source intensity may be used for detection, thus increasing the overall performance of the apparatus.

All these objects are met by an interferometric apparatus for monitoring changes of the refractive index of fluid samples in capillary tubes which comprise a source of coherent light, preferably a diode laser, which is arranged such with respect to a capillary tube with a bore being part of a capillary liquid chromatographic system or of a capillary electrophoretic system, that said coherent light beam strikes said bore of said capillary tube about perpendicular to its longitudinal extension, and, in forward direction of said coherent light beam, behind said capillary tube a photoelectric detector for monitoring a resulting interference fringe pattern and shifts thereof, which is connected to an evaluation electronics. Between said light source and said capillary tube there is arranged a beam splitting optical element for generating a converging probe beam which travels along a probe beam axis and strikes said capillary bore, and a converging reference beam which is travelling along a reference beam axis, that extends generally parallel to said probe beam axis and is located in close vicinity to it, and which does not strike said capillary bore. Preferred embodiments of the invention are subject of the respective dependent patent claims.

BRIEF DESCRIPTION OF THE DRAWINGS

Further objects will become apparent from the description of exemplary embodiments of the invention with reference to the accompanying drawings in which.

DETAILED DESCRIPTION OF PREFERRED EMBODIMENTS OF THE INVENTION

Figure 1:
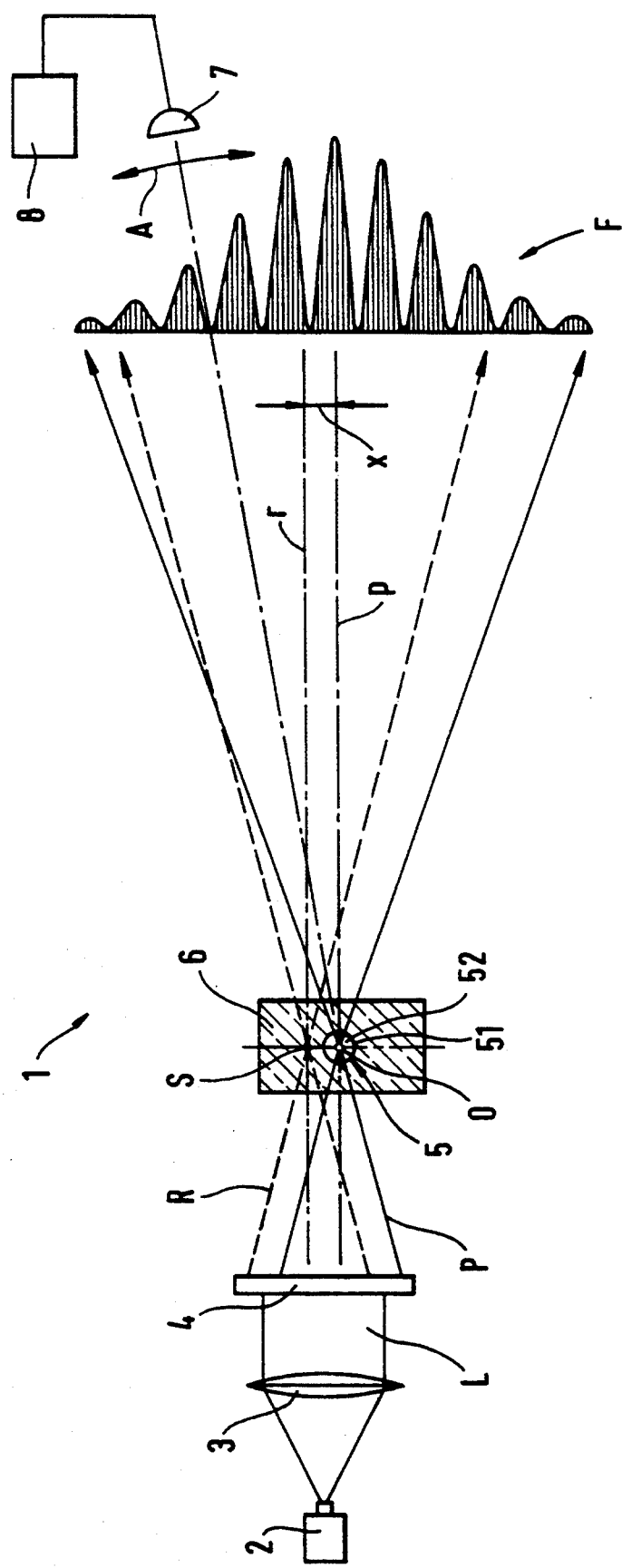
FIG. 1 is a schematic representation of a first embodiment of an interferometric apparatus according to the invention.

In the schematic representation in FIG. 1, a first exemplary embodiment of an interferometric apparatus for monitoring changes of the refractive index of a fluid sample is designated reference numeral 1. The interferometric apparatus 1 comprises a source 2 of coherent light L, preferably a laser diode, which is arranged such with respect to a capillary tube 5, having a bore 52, that is part of a capillary chromatographic system or of a capillary electrophoretic system, that the laser beam L strikes the capillary tube 5 about perpendicular to its longitudinal extension. In the schematic drawing of FIG. 1 the longitudinal extension of the capillary tube having a central bore of a certain diameter 5 is perpendicular to the drawing plane. An optical lens system 3 is arranged in the light path after the laser source 2 and focusses the laser beam L in the desired manner. In the forward direction of the laser beam L, behind the capillary tube 5, there is arranged a photoelectric detector 7 for monitoring an interference fringe pattern F resulting from the light coming from the capillary tube 5. Preferably the photoelectric detector 7 is a position sensitive diode, which is located on or near the laser beam axis. Upon changes of the refractive index of the fluid sample in the capillary tube the interference fringe pattern is changed and shifted. The changes of the fringe pattern are indicated in FIG. 1 by the double arrow A. The photoelectric detector, which is sensitive to the changes and shifts of the interference fringe pattern is also connected to an evaluation electronics 8 for amplification, transformation and evaluation of the signals produced by the photoelectric detector 7 in response to the detected changes in the interference fringe pattern.

In order to reduce the complexity of the interference fringe pattern F and in order to enhance the signal/-noise ratio of the interferometric apparatus in the exemplary embodiment according to the invention depicted in FIG. 1 the capillary tube 5 is surrounded by a material 6, which has good transmissivity for the laser light L provided, and which has a refractive index approximately or completely matching the refractive index of the walls 51 of the capillary tube 5. So far the interferometric apparatus 1 for monitoring changes of the refractive index of fluid samples corresponds to the interferometric apparatus described in Analytical Chemistry, 1991, Vol.63, No.23, page 2689.

In contrary to the prior art apparatus, in the interferometric apparatus according to the present invention the probe beam P and the reference beam R are not produced at the capillary tube (e.g. the reference beam R by total reflection at the walls 51 of the capillary tube). Instead, the laser beam L generated by the laser source 2 is directed at a beam splitting optical element 4, which is arranged in the light path between the source 2 and the capillary tube 5. The beam splitting optical element 4 generates two converging laser beams, the probe beam P travelling along a probe beam axis p, which intersects the capillary bore 52 about perpendicular to its longitudinal extension, and the reference beam R, travelling in close vicinity of the probe beam P along a reference beam axis r, without striking the bore 52. The reference beam axis r extends generally parallel to the probe beam axis p and is separated from the probe beam axis p by a distance x, which is greater than the radius of the bore 52 of the capillary tube 5, but amounts to less than about 20 times the radius of the bore 52 of the capillary tube 5.

The arrangement of the beam splitting optical element 4 in the path of the laser beam L from the laser source 2 is such, that the generated converging probe beam P has a waist 0, whose narrowest portion is preferably located within the capillary bore 52 in such a way, that most of its intensity transverses the bore 52 preferably along its center. The generated converging reference beam R has a waist S, which is located such, that its waist does not strike the capillary bore 52 and that most of its intensity does not interact with the bore 52. The waists 0 and S of the probe beam P and of the reference beam R, respectively, have narrowest portions which are smaller than the radius of the bore 52 of the capillary tube 5. Preferably the intensities of the probe beam P and of the reference beam R are of about comparable magnitude.

The diameters of the bores of the capillary tubes 5 used in capillary chromatographic systems or in capillary electrophoretic systems amount about 1 $\mu m$ to about 500 $\mu m$. The preferred diameters amount about 5 $\mu m$ to about 50 $\mu m$, in particular to less than about 25 $\mu m$.

The criteria which the beam splitting optical element 4 must meet are, that it must be able to generate two converging generally parallel extending coherent light beams from a coherent light beam; the axis of the two generated beams must be located in close vicinity to each other, in order to have external perturbations, such as for example inhomogenities in the temperature of the surrounding environment, act on both beams in the same manner; the shapes of the wavefronts of the two generated converging light beams shall correspond to each other, preferably the beams have Gaussian properties. Thus, the beam splitting optical element 4 can be a diffractive element.

Preferably the diffractive element has focussing properties such, that the probe beam P and the reference beam R, respectively, are focussed without the need of additional lenses or the like optical elements.

In the most preferred embodiment of the apparatus according to the present invention the diffractive element 4 is a holographically recorded optical element (HOE), or a computer-generated hologram (CGH) or a binary or a multilevel of a continuous surface relief element, or a combination of them.

The illuminating system 2, 3, 4 of the interferometric apparatus 1 according to the invention generates two converging beams of coherent light with similar, preferably Gaussian, wavefronts, a probe beam P, which strikes the capillary bore 52, and a reference beam R, which does not strike the capillary bore 52. The probe beam P and the reference R beam extend in close vicinity of each other, so that external perturbations, such as for example temperature gradients in the surrounding environment, vibrations, etc., influence both beams in the same manner. The diameters of the waists of the beams P, R are smaller than the radius of the bore 52 of the capillary tube 5. The probe beam passes through the test sample flowing through the capillary tube 5 and is modified by it. The reference beam passes close to the capillary bore 52 but does not strike it and thus remains unaltered. In forward direction of the beam paths, behind the capillary tube 5, the superposition of the probe beam P and the reference beam R results in a interference fringe pattern F, whose changes are monitored by the photoelectric detector 7. The signals produced by the photoelectric detector 7 are amplified, transformed and evaluated by the evaluation electronics 8.

A change of the refractive index of the test sample flowing through the bore 52 of the capillary tube 5 induces a change of the phase of the probe beam P. The change of the phase of the probe beam P results in a modification of the interference fringe pattern F, usually the fringes are displaced for a small distance in one direction. All fringes of the original interference fringe pattern F are equally displaced. This makes the monitoring of the changes of the interference pattern F with the photoelectric detector 7 particularly easy. From the detection of the shifts of the interference fringe pattern the phase change of the probe beam P is deducted.

The phase change of the probe beam P in turn is linearly related to the change of the refractive index of the fluid test sample. Therefore, the monitoring of the changes of the interference fringe pattern F allows an easy monitoring of the refractive index changes of a test sample flowing through the capillary tube 5.

Figure 2:
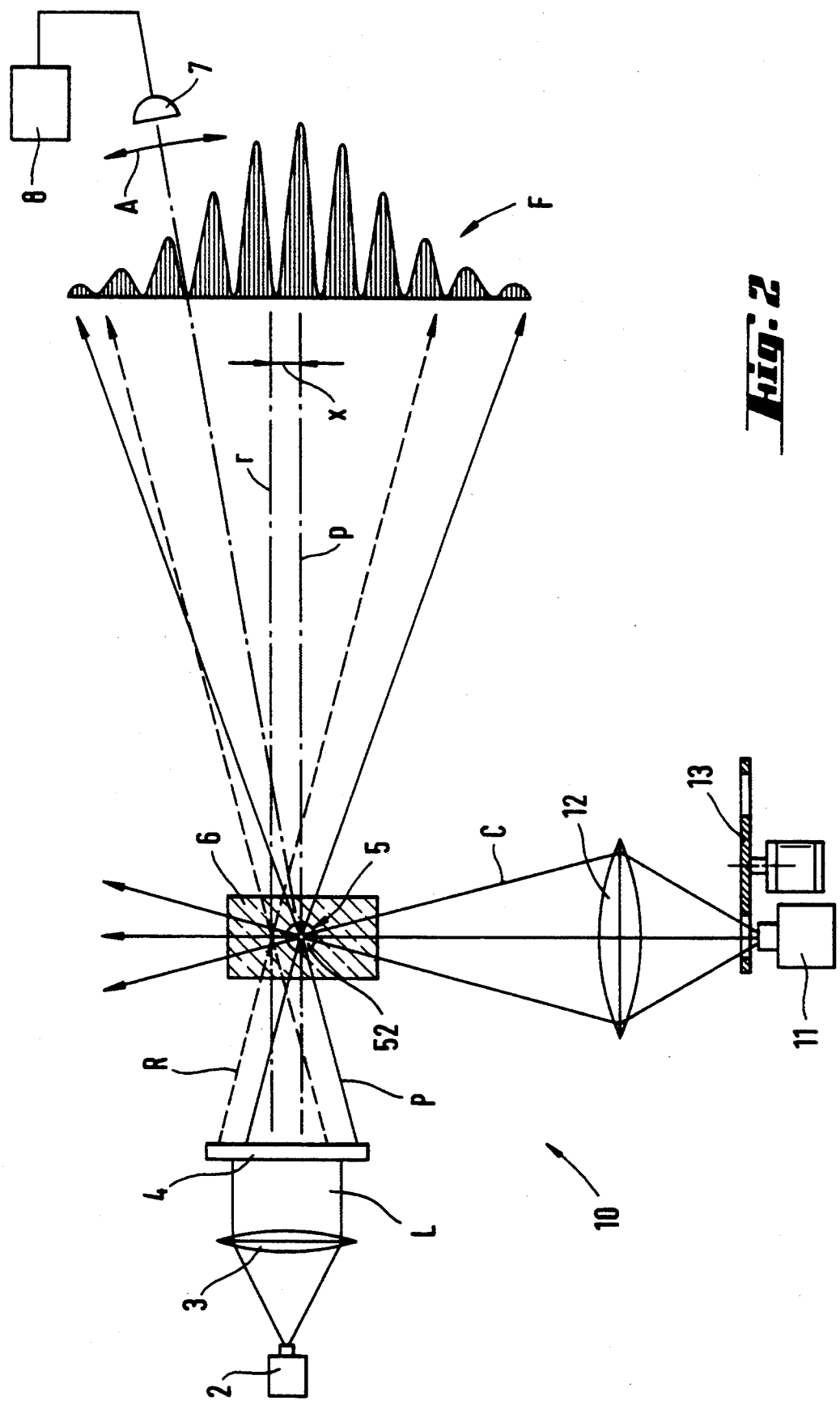
FIG. 2 is a schematic representation of a second embodiment of the interferometric apparatus according to the invention.

In FIG. 2 the setup of a second exemplary embodiment of the interferometric apparatus according to the invention is schematically depicted and attributed reference numeral 10. This embodiment of the present invention is designed for indirect thermo-optical absorption measurements through indirect laser induced refractive index changes. In addition to the setup of the interferometric apparatus 1 according to FIG. 1 it comprises a pump laser 11, which is arranged such, that the pump laser beam C intersects the bore 52 of the capillary tube 5 in the interaction region of the probe beam P with the test sample flowing through the bore 52 of the capillary tube 5 and about perpendicular to the probe beam axis p and to the longitudinal extension of the capillary tube 5. An optical lens system 12 is arranged in the path of the pump laser beam C, such that the beam C is focussed on the bore of the capillary tube 5. The pump laser 11 is intensity modulated. The intensity modulation is accomplished by using a pulsed laser source, or an intermittently operated driving power supply. A preferred and easy mode for the intensity modulation of the pump laser is the use of a chopper 13, which is arranged in the path of the pump laser beam C between the pump laser 11 and the capillary tube 5.

According to the absorbance properties of the test sample to be analyzed and to the known absorbance properties of a solvent flowing through the capillary tube 5, energy from the pump laser beam C is absorbed. The absorbed energy is immediately released again in the form of radiative emissions, in the form of fluorescence and/or phosphorescence, and in the form of non-radiative transitions, mainly molecular rotations and translations. The non-radiative part of the absorbed energy is transferred immediately to the solvent, which changes its temperature in a modulated fashion at the same frequency as the modulation frequency of the pump laser 11. The periodic changes of the temperature of the solvent result in periodic changes of the refractive index of the solvent, according to its specific $dn/dT$, where n stands for the refractive index, T stands for the Temperature, and dn and dT stand for the respective changes. The laser-induced periodic changes of the refractive index are monitored as described hereinbefore and evaluated.

While the present invention has been illustrated by example of capillaries with bores of generally circular cross-sections, it is to be understood, that capillaries having a bore with square or rectangular cross-sections can equally well be used. In that instance, the radius of the capillary bore 52 is defined as half the width of its smallest side.

The advantages of the interferometric apparatus for monitoring changes of the refractive index of fluid samples in capillary tubes, according to the present invention are apparent. The reference beam and the probe beam are generated independent from the capillary tube by a separate beam splitting optical element, preferably by a holographic element, so irregularities on the surface of the capillary tube cannot any more modify the reference beam in an unexpected manner. The two beams are spaced apart only by a small distance, so external perturbations, such as for example temperature gradients of the surrounding environment or vibrations, etc., effect both beams in the same manner. The shapes of the wavefronts of the reference beam and of the probe beam are the same, preferably they are Gaussian. The sensitivity of the individual fringes of the interference fringe pattern with respect to changes of the refractive index of the test sample flowing through the capillary tube is identical for all fringes. Upon changes of the refractive index of the test sample all fringes of the interference fringe pattern are equally displaced in one direction only. All the light striking the capillary tube, including the light travelling along the probe beam axis can be used, thus increasing the resolution and the overall performance of the interferometric apparatus for monitoring refractive index changes of fluid samples.

What is claimed is:

1. An interferometric apparatus for monitoring changes of the refractive index of fluid samples in capillary tubes, which comprises a source of coherent light, which is arranged with respect to a capillary tube having a bore, which capillary tube is part of a capillary liquid chromatographic system or of a capillary electrophoretic system, such that a coherent light beam, which is produced by the source of coherent light, strikes said capillary tubes about perpendicular to its longitudinal extension, and, in the forward direction of said coherent light beam, behind said capillary tube, a photoelectric detector for monitoring a resulting interference fringe pattern and shifts thereof, which photoelectric detector is connected to an evaluation electronics, wherein there is arranged between said light source and said capillary tube a beam splitting optical element for generating a converging probe beam which travels along a probe beam axis and strikes said capillary bore, and a converging reference beam which travels along a reference beam axis, that extends generally parallel to said probe beam axis and is located in close vicinity to said probe beam axis, and which does not strike said capillary bore.

2. An apparatus according to claim 1, wherein said beam splitting optical element is arranged in the path of propagation of said coherent light beam between said light source and said capillary tube, the bore of which has an internal radius, such that said converging probe beam has a waist which is located within said bore of said capillary tube, and that the reference beam has a waist which is located in close vicinity of said capillary tube without striking said bore.

3. An apparatus according to claim 2, wherein said converging probe beam has a diameter that is smaller than said radius of said capillary bore and a substantial part of the intensity of said probe beam transvering said capillary bore, and wherein said reference beam has a diameter which about corresponds to that of said probe beam, and wherein the reference beam intensity substantially avoids impacting on said capillary bore.

4. An apparatus according to claim 2, wherein said probe beam axis and said reference beam axis are separated by a distance, which is greater than said radius of said bore of said capillary tube, but amounts to less than about 20 times said bore-radius.

5. An apparatus according to to claim 4, wherein at least that part of said capillary tube which is struck by the probe beam is surrounded by a light transmissive material whose refractive 6. An apparatus according to claim 2, wherein said bore of said capillary tube has a diameter of from about 1 $\mu$m to about 500 $\mu$m. index approximately matches or totally matches a refractive index of the capillary tube.

7. An apparatus according to claims 6, wherein said probe beam and said reference beam have wavefronts of similar shapes and intensities.

8. An apparatus according to claim 1, wherein said beam splitting optical element is a diffractive element.

9. An apparatus according to claim 8, wherein said diffractive element has focussing properties.

10. An apparatus according to claim 9, wherein said diffractive element is a holographically recorded optical element, a computer-generated hologram or a binary or a multilevel of a continuous surface relief element, or a combination of them.

11. An apparatus according to claim 10, wherein there is arranged a pump laser such, that a pump laser beam intersects said capillary tube in an interaction region of said probe beam with a sample flowing through said capillary tube, and about perpendicular to said probe beam axis and to a longitudinal extension of said capillary tube.

12. An apparatus according to claim 11, wherein said pump laser is intensity modulated, by using a pulsed laser source, or an intermittendly operated driving power supply, or by arranging a chopper (13) in the path of said pump laser beam between said pump laser and said capillary tube.

13. Apparatus according to claims 2, wherein said capillary bore has a square or a rectangular cross-section, and further wherein said radius of said bore is defined as half the width of the smallest side of said capillary bore.

14. An apparatus of claim 1 wherein the source of coherent light is a diode laser.

15. An apparatus of claim 6 wherein said diameter of said capillary tube is from about 5 $\mu$m to about 50 $\mu$m.

16. An apparatus of claim 15 wherein said diameter of said capillary tube is less than about 25 $\mu$m.

* * * * *